United States Patent [19]

Krall et al.

[11] 4,057,581

[45] Nov. 8, 1977

[54] PROCESS FOR PREPARING DIPHENYLAMINES

[75] Inventors: Hermann-Dieter Krall, Meerbusch; Oskar Weissel; Hans-Helmut Schwarz, both of Krefeld, all of Germany

[73] Assignee: Bayer Aktiengesellschaft, Leverkusen, Germany

[21] Appl. No.: 677,478

[22] Filed: Apr. 15, 1976

[30] Foreign Application Priority Data

May 10, 1975 Germany .................. 2520893

[51] Int. Cl.² .............. C07C 87/54; C07C 91/16; C07C 91/18
[52] U.S. Cl. ..................... 260/571; 252/465; 252/470; 252/471; 252/472; 252/474; 260/576
[58] Field of Search .............. 260/571, 576; 252/470

[56] References Cited

U.S. PATENT DOCUMENTS 3,953,508  4/1976  Kalopissis et al. ................ 260/571

FOREIGN PATENT DOCUMENTS 1,382,206  1/1975  United Kingdom ................ 260/576
1,362,284  8/1974  United Kingdom ................ 252/470
1,362,285  8/1974  United Kingdom ................ 252/470

*Primary Examiner*—Daniel E. Wyman
*Assistant Examiner*—John J. Doll
*Attorney, Agent, or Firm*—Burgess, Dinklage & Sprung

[57] ABSTRACT

Diphenylamines having the formula:

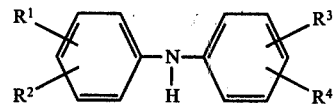

wherein
$R^1$, $R^2$, $R^3$ and $R^4$ are the same or different and are hydrogen, alkyl with up to 4 C atoms or alkoxy with up to 4 C atoms, are prepared by catalytically dehydrogenating the corresponding wholly or partially hydrogenated diphenylamines. The catalyst used is a nickel/chromium catalyst containing manganese and/or aluminum and/or copper and/or sulphates of the alkali metals or alkaline earth metals.

18 Claims, No Drawings

PROCESS FOR PREPARING DIPHENYLAMINES

BACKGROUND

This invention relates to a process for the production of diphenylamine and its derivatives by dehydrogenation of wholly or partially hydrogenated diphenylamine and its derivatives in the presence of nickel/chromium catalysts.

Diphenylamine is of considerable industrial importance. It is known from German Published Pat. No. 2,331,878 to prepare diphenylamine and its derivatives by dehydrogenation of N-cyclohexylidene-aniline and its derivatives in the presence of a nickel catalyst on alumina or of a CuO—$Cr_2O_3$ catalyst on $SiO_2$. The catalysts however proved to have a low stability so that the yield of diphenylamine already drops down sharply after a few hours.

SUMMARY

This invention provides more suitable catalysts for the production of diphenylamine and its derivatives by catalytic dehydrogenation of N-cyclohexalidene-aniline and other wholly or partially hydrogenated diphenylamines and their derivatives.

It has now been found that diphenylamines of the formula:

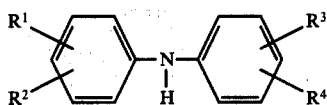 (I)

in which:
R$^1$, R$^2$, R$^3$ and R$^4$ are identical or different and represent hydrogen, alkyl radicals with up to 4 C atoms or alkoxy radicals with up to 4 C atoms,
are obtained in good yield and with high selectivity by catalytic dehydrogenation of the corresponding wholly or partially hydrogenated diphenylamines using a nickel/chromium catalyst containing also manganese and/or aluminium and/or copper and/or sulphates of the alkali metals or alkaline earth metals.

DESCRIPTION

Alkyl radicals which may be mentioned are methyl, ethyl, propyl, isopropyl, butyl, isobutyl and tert.-butyl radicals, preferably methyl and ethyl radicals.

Alkoxy radicals which may be mentioned are methoxy, ethoxy, propoxy, isopropoxy, butoxy, isobutoxy and tert.-butoxy radicals, preferably methoxy and ethoxy radicals.

The starting materials for the process according to the invention are known or can be prepared analogously to processes known from the literature.

Preferred starting materials for the process according to the invention are N-cyclohexylidene-aniline and other wholly or partially hydrogenated diphenylamines.

Examples of such wholly or partially hydrogenated diphenylamines which may be mentioned are dicyclohexylamine, N-cyclohexylidene-cyclohexylamine and N-cyclohexyl-aniline; N-cyclohexylidene-aniline may be mentioned in particular.

The preferred starting materials for the process according to the invention are readily available; N-cyclohexylidene-aniline and N-cyclohexylidene-cyclohexylamine are obtained according to known methods in very good yields from cyclohexanone and aniline or, respectively, cyclohexylamine; N-cyclohexyl-aniline and dicyclohexylamine can also be obtained easily according to known processes, for example from the same starting materials by hydrogenating alkylation.

Mixtures of the said compounds are also suitable as starting materials for the process to the invention. Particularly a mixture obtained by continuous operation of the process according to the invention which, after separating off the diphenylamine, contains, in addition to unreacted starting material and small amounts of other by-products, the abovementioned compounds corresponding to the starting material used, can also be used advantageously in the process according to the invention.

In general, the process according to the invention is carried out in a temperature range from about 250° to about 400° C, preferably between about 280° and about 370° C and especially in the range from about 300° to 350° C.

The process according to the invention is generally operated under normal pressure but it is also possible to work under reduced or elevated pressure, especially in the range from 0.1 to 3.0 bars.

The selection of the dehydrogenation catalyst is particularly important for the process according to the invention.

Dehydrogenation catalysts used in the process according to the invention are catalysts which contain nickel and chromium and also contain manganese and/or aluminium and/or copper and/or sulphates of the alkali metals or alkaline earth metals.

A group of catalysts according to the invention are nickel/chromium catalysts which also contain aluminium, copper and sulphates of the alkali metals and/or alkaline earth metals, the ratios by weight of the metals nickel, chromium, aluminium, copper and the alkali metals and/or alkaline earth metals to one another being about 40 to 60:6.8 to 17.5:1.5 to 8.0:0.05 to 1.0:0.5 to 7.0.

A preferred group of these catalysts according to the invention is known from German Published Pat. No. 2,049,809. They contain nickel, chromium, aluminium, copper and alkali metal in a ratio of the metals of 40 to 60:6.8 to 17.1:1.6 to 8.0:0.05 to 1.0:0.65 to 3.4 and are prepared by adding an alkali metal compound to the catalyst base composition containing nickel, chromium, aluminium and copper, which is obtained by precipitation, subsequently drying and shaping the mixture, reducing at elevated temperature with hydrogen and, optionally, subsequently treating with $CO_2$ under hot conditions, by a. impregnating the base composition with the appropriate amount of alkali metal sulphate as the alkali metal compound, b. shaping the impregnated and dried catalyst composition to give shaped articles with a bulk density of 0.8 to 1.6 g/ml, c. reducing the resulting catalyst mouldings at temperatures between 350° and 420° C, first with about half to about twice the equivalent amount of hydrogen calculated for reduction of the nickel compounds to metallic nickel and if appropriate of the chromium-VI compounds to compounds of trivalent chromium in the course of 1 to 4 hours and d. either, at the earliest 1 week after process stage (c), further reducing the catalyst mouldings with about 2 to 10 times the equivalent amount of hydrogen calculated for reduction of the nickel compounds of the catalyst to metallic nickel, in the course of 1 to 4 hours at temperatures between 350° and 420° C until the content of metallic nickel in the catalyst is about 10 to 35 percent by weight, or stabilising the catalyst mouldings after process stage (c), grinding and reshaping to give mouldings with a bulk density of 0.8 to 1.6 g/ml and then further reducing these with about 2 to 10 times the equivalent amount of hydrogen calculated for reduction of the nickel compounds of the catalyst to metallic nickel, in the course of 1 to 4 hours at temperatures between 350° and 420° C until the content of metallic nickel in the catalyst is about 10 to about 35 percent by weight.

A further preferred group of these catalysts according to the invention is known from German Published Application No. 2,146,052. They are prepared in a manner analogous to that used for the catalysts described above and known from German Published Pat. No. 2,049,809, the difference being that the reduction is carried out until the content of metallic nickel in the catalyst is about 35 to about 45, preferably about 42,% by weight.

The catalysts according to the invention which contain alkaline earth metal sulphate in place of alkali metal sulphate can also be prepared in the same way. Alkaline earth metals which may be mentioned are magnesium, calcium, strontium and barium, preferably magnesium.

A further group of catalysts according to the invention are nickel/chromium mixed catalysts with added manganese and/or aluminium, in which the metals nickel, chromium, manganese and aluminium are present in a ratio of about 10 to 50: about 4 to 15: about 1 to 30: about 0 to 5.

The preparation of these catalysts can be carried out according to methods which are in themselves known. Advantageously, an aqueous solution containing nickel, chromium, manganese and optionally aluminium in the form of their watersoluble salts, for example nitrates, is used as the starting material and the mixture of the corresponding hydroxides and/or carbonates is precipitated from this solution by adding alkali metal hydroxide, bicarbonate or carbonate, or ammonia. Of course, it is also possible to use a mixture of the said precipitants for precipitation. Preferably, the alkali metal hydroxides, bicarbonates and carbonates used are the corresponding compounds of potassium and especially of sodium. The chromium salt used can also be a compound of 6-valent chromium (see, for example, Handbook of Catalysis, volume VIII, 1st half, page 674 (1943) and Houben-Weyl, volume IV/2, page 137 et seq. (1955)). The state of the art relating to the use of sodium hydroxide solution, ammonia, alkali metal carbonates and alkali metal bicarbonates is described, for example, in Houben-Weyl, volume IV/2, page 137 et seq. (1955) and Handbook of Catalysis, volume V (Heterogeneous Catalysis II, page 412 et seq. (1943). Depending on the conditions of precipitation, that is to say on the precipitant used, the pH value of the solution and the nature of the chromium compound employed, the nickel is obtained, for example, as the hydroxide, as the basic carbonate (see, for example, Gmelin, 8th edition, part B, issue 3, system No. 57, (1966), page 846 to 853), or as ammonium nickel chromate (see Gmelin, 8th edition, part B, issue 3, System No. 57, page 1,215 to 1,216 (1966)). A further possible variant for the preparation of the abovementioned precipitate is, for example, to precipitate a carbonate/hydroxide mixture from a solution of a nickel salt, manganese salt and optionally an aluminium salt using alkali metal carbonate solution and, after rinsing with water, to react this mixture with ammonium bichromate at elevated temperature, in a manner which is in itself known.

The precipitate which is thus obtained, as the catalyst base composition, in a manner which is in itself known, for example as described above, is then washed, dried, shaped and reduced with hydrogen at elevated temperature in a manner which is in itself known.

Using the dehydrogenation of N-cyclohexylidene-aniline as an example, the reaction according to the invention is illustrated by the following equation:

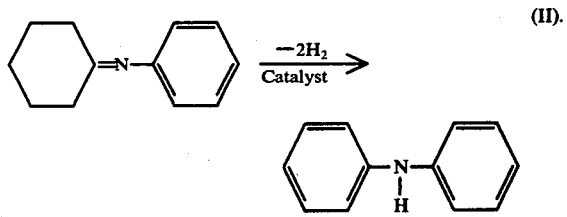

(II).

In general, the process according to the invention is carried out in such a way that the starting material, optionally together with an inert gaseous diluent, is passed over the catalyst in the temperature range mentioned above and under the abovementioned pressure.

Gaseous diluents which may be used are, advantageously, anhydrous or substantially anhydrous gases which are inert under the reaction conditions, such as hydrogen, methane or natural gas, but especially dry nitrogen; it is appropriate to use gases which are anhydrous or substantially anhydrous in order to prevent hydrolysis of the starting material, for example N-cyclohexylidene-aniline. It is also advantageous to work with exclusion of oxygen.

The amount of the gaseous diluent or carrier gas is generally about 0.1 to about 10.0, preferably about 1.0 to about 5.0 and especially 1.5 to 2 mols per mol of the starting compound or starting compounds.

In general, the process according to the invention is carried out at a catalyst load of about 0.05 to about 0.5, preferably from about 0.1 to about 0.4, and especially from about 0.2 to about 0.3 (g of starting material per ml of catalyst and per hour).

The process according to the invention is generally carried out continuously, especially for economic reasons; the particular design of the reactor is not an essential part of the invention; this reactor can be designed in a manner which is in itself known in accordance with the state of the art, for example a reaction tube or a tubular converter with the catalyst in the tubes can be employed as the reactor.

For example, it is possible to evaporate the starting material used in a dry stream of nitrogen, to heat this gaseous feed stream to a reaction temperature of, for example, 320° C and to pass it at this temperature through a tubular converter at a catalyst load of, for example, 0.1 to 0.4 (g of starting material per ml of catalyst and per hour); subsequently, the reaction product can be cooled, for example, to a temperature between 100° and 250° C, fed into a continuously operated distillation unit and separated by distillation under normal pressure or under reduced pressure of, for example 0.1 bar, and diphenylamine can be taken off, for example at the top, and the mixture of unreacted starting material and by-products formed in the reaction, as well as the carrier gas, can be withdrawn, if necessary after separating off the hydrogen formed, and recycled into the reaction.

It can, however, also be advantageous to separate the reaction mixture, after cooling, into a liquid phase, essentially containing diphenylamine, and into a gaseous phase, which essentially contains the carrier gas and the hydrogen formed during the reaction. By cooling this stream of gas to temperatures of, for example, below 50° C, it is possible to separate off high-boiling by-products, like aniline, N-cyclohexyl-aniline and N-cyclohexylidene-aniline, in a liquid form and then to recycle them into the reaction, or to separate them, for example by distillation, for an appropriate utilisation of the individual compounds. The gas which leaves the separator can, for example, be recycled into the reaction as the carrier gas, as described above, or, advantageously, because of its high calorific value, can be used directly or indirectly for heating the reactor.

However, working up of the reaction product in order to obtain the diphenylamine, which is obtained after separating off the carrier gas and the hydrogen formed, can also be carried out in a known manner by crystallisation from a solvent such as methanol.

By-products which can be formed in the process according to the invention are, in addition to the partially hydrogenated diphenylamines formed by partial dehydrogenation of the starting material, also benzene, aniline and carbazole; of these aniline can be employed again for the preparation of the starting material for the process according to the invention, whilst benzene and carbazole can be used as such. 4-Aminodiphenyl is formed in the process according to the invention in the order of magnitude of 1 ppm.

The technical advance of the process according to the invention may be summarized as follows.

The catalysts according to the invention exhibit a high mechanical stability and a long life.

The degree of conversion and the selectivity during the life time of the catalysts according to the invention are also high. It is true that these do decrease somewhat with regard to the desired product but the formation of by-products which cannot be re-used as starting materials is virtually independent of time in the process according to the invention, whilst the formation of by-products which can be used again as starting material increases. Since these by-products can be recycled into the desired reaction and so are not lost to the reaction, the advantage of the long life of the catalyst outweighs the slight reduction in its activity and selectivity. Accordingly, a selectivity of the catalyst of more than 90% can be assumed for virtually its entire life.

Furthermore, there are virtually no corrosion problems, such as are known from the customary preparation of diphenylamine from aniline with acid catalysts. Therefore, commercially available steels, for example normal C steel, can be used as the material for the equipment used for carrying out the process according to the invention, especially for the reactor.

EXAMPLE 1

A catalyst base composition containing 38.2% by weight of nickel, 8.9% by weight of chromium, 3.2% by weight of aluminium and 0.2% by weight of copper was prepared according to the instructions of DT-AS (German Published Specification) No. 2,049,809; 12,870 parts by weight of this composition were stirred with a solution of 337.5 parts by weight of potassium sulphate in 11,700 parts by weight of water and the mixture was dried and ground. The catalyst composition thus obtained was mixed with 1.5% of its weight of graphite and shaped under a moderate moulding pressure to give cylinders 5 mm in diameter and 5 mm in height. These cylinders were treated for 2.5 hours at about 390° C with 100 parts by volume of hydrogen per part by weight of catalyst and per hour. After cooling to room temperature, the cylinders were treated with ammonia and then with carbon dioxide, until the exothermic effects which arises had subsided. They were then ground and, together with 3% of their weight of graphite, shaped again under a higher moulding pressure to give cylinders of the abovementioned size. The moulded catalyst was finally treated for 2.5 hours at about 390° C with 725 parts by volume of hydrogen per part by weight of catalyst and per hour and then heat-treated for 30 hours at about 100° C in a stream of carbon dioxide. The catalyst thus obtained has a bulk density of 1.2 g per ml and contains 26.6% by weight of metallic nickel for a total nickel content of 51.6% by weight.

EXAMPLE 2

The amounts of starting material and the volumes of inert gas indicated in the following examples were fed into a reaction tube with a diameter of 17 mm and a length of about 500 mm, the upper part of which is used as an evaporating zone and the lower part of which is filled with 30 ml of the catalyst obtained according to Example 1. The reaction mixture leaves the reaction tube at the lower end and, after cooling and gas/liquid phase separation, is worked up in a known manner by distillation or crystallisation or is analysed by gas chromatography.

The amounts and volumes indicated in each case were measured at room temperature, the volumes were measured by means of rotameter and the feed rates are given in grams per hour or, respectively, in 1 per hour.

EXAMPLE 2.1

3.0 g of N-cyclohexylidene-aniline and 1.0 l of nitrogen were metered into the reactor described in Example 2; the catalyst temperature was kept at about 320° C. After a start-up period of a few days, a reaction product which consists to the extent of 89.6% by weight of diphenylamine is obtained, the relative degree of conversion being 99%.

The product also contains 2.1% by weight of benzene, 2.5% by weight of aniline, 4.6% by weight of N-cyclohexyl-aniline and 0.3% by weight of carbazole as well as 0.9% by weight of other impurities; the 4-aminodiphenyl content in the crude product is 1 ppm.

The yield of diphenylamine thus corresponds to about 95% of theory, based on the amount of aniline which was employed for the virtually quantitative conversion to N-cyclohexylidene-aniline.

After a running period of 5,000 hours, the reaction product contained 85% by weight of diphenylamine, whilst the amounts of the by-products benzene, aniline and carbazole were virtually unchanged. On the other hand, the concentration of N-cyclohexyl-aniline, which can be used again, and of unreacted N-cyclohexylidene-aniline had risen to about 10% by weight. The concentration of 4-aminodiphenyl in the reaction product had not changed.

EXAMPLE 2.2 a. 9.0 g of N-cyclohexylidene-aniline and 8.5 l of nitrogen were metered into the reactor described in Example 2, the catalyst temperature being 320° C. After a reaction time of 94 hours, the reaction product contained 92.8% by weight of diphenylamine, 0.3% by weight of N-cyclohexylidene-aniline, 0.3% by weight of N-cyclohexyl-aniline, 1.4% by weight of benzene and 5.1% by weight of aniline.

b. After a running period of 286 hours, the feed mixture was reduced to 6.0 g of N-cyclohexylidene-aniline per hour and 5.5 l of nitrogen per hour. After 958 hours, the reaction product consisted of 91.1% by weight of diphenylamine, 3.0% by weight of N-cyclohexylidene-aniline, 1.0% by weight of N-cyclohexyl-aniline, 0.7% by weight of benzene and 4.2% by weight of aniline.

c. After the catalyst had been in operation for 1,507 hours, the feed mixture was changed again, the amount of nitrogen being reduced to 4.2 l per hour. After a total running period of 1,800 hours, the reaction mixture had the following composition: 91.2% by weight of diphenylamine, 0.2% by weight of N-cyclohexylidene-aniline, 1.2% weight of N-cyclohexyl-aniline, 1.5% by weight of benzene and 5.2% by weight of aniline, as well as 0.7% by weight of several other substances.

EXAMPLE 2.3

3.0 g of N-cyclohexylidene-aniline and 5.0 l of nitrogen were metered at the temperature indicated in Table I which follows, into the reactor described in Example 2. The composition of the reaction product is also given in this table.

Table 1

| | Reaction product (% by weight) | | | | | |
|---|---|---|---|---|---|---|
| Temperature (°C) | Diphenyl-amine | N-Cyclohexylidene-aniline | N-Cyclohexyl-aniline | Aniline | Carbazole | Remainder (several substances) |
| 280 | 69 | 22 | 5 | 2 | 1 | 1 |
| 300 | 88 | 5 | 2 | 4 | 1 | — |
| 320 | 92 | 1 | 2 | 4 | 1 | — |
| 350 | 89 | 0.2 | — | 4 | 5 | 1.8 |
| 370 | 86 | 0.2 | — | 5 | 7 | 1.8 |
| 390 | 83 | 0.1 | — | 4 | 12 | 0.9 |

EXAMPLE 2.4

The amount of N-cyclohexylidene-aniline indicated in Table II which follows and 5.0 l of nitrogen are fed into the reactor described in Example 2, the reaction temperature being 325° C. The composition of the reaction product obtained in each case is also given in Table II.

Table II

| | Reaction product (% by weight) | | | | |
|---|---|---|---|---|---|
| N-Cyclohexylidene-aniline (g/h) | Di-phenyl-amine | N-Cyclohexyl-aniline | Aniline | Carbazole | Remainder (several substances) |
| 5.1 | 93 | — | 4 | 2 | — |
| 5.7 | 94 | — | 3 | — | 1.0 |
| 7.2 | 92 | 1 | 3 | 0.1 | 0.9 |
| 8.4 | 88 | 3 | 4 | — | 1.0 |
| 9.9 | 85 | 6 | 4 | — | 1.0 |

EXAMPLE 2.5

6.6 g of N-cyclohexylidene-aniline and the amount of nitrogen indicated in Table III which follows were charged to the reactor described in Example 2, the reaction temperature being 320° C. The composition of the reaction product obtained in each case can also be seen in Table III which follows.

Table III

| | Reaction product (% by weight) | | | | | |
|---|---|---|---|---|---|---|
| Nitrogen (l/h) | Di-phenyl-amine | N-Cyclohexylidene-aniline | N-Cyclohexyl-aniline | Aniline | Carbazole | Remainder (several substances) |
| 5 | 91 | 0.1 | 1 | 6 | 1 | 0.9 |
| 2 | 90 | 0.1 | 3 | 6 | 0.9 | — |
| 0 | 85 | 0.1 | 3 | 9 | 2.9 | 0 |

EXAMPLE 2.6

6.0 g of N-cyclohexylidene-aniline and 2.0 l of hydrogen are metered into the reactor described in Example 2, the catalyst temperature being 350° C.

Under these conditions the catalyst has a life time of more than 6,000 hours. Table IV which follows gives the relative degree of conversion and the main constituents of the resulting reaction mixture as a function of the running time of the catalyst.

Table IV

| | | Reaction product (% by weight) | | | |
|---|---|---|---|---|---|
| Running time (hours) | Relative degree of conversion (%) | Di-phenyl-amine | N-Cyclohexylidene-aniline | N-Cyclohexyl-aniline | Aniline |
| 3,000 | 98.5 | 80 | 1.3 | 1.1 | 8.5 |
| 4,000 | 98.0 | 80 | 0.9 | 4.4 | 8.2 |
| 5,000 | 95.0 | 76 | 3.7 | 7.0 | 7.4 |
| 6,000 | 88.0 | 73 | 6.4 | 6.5 | 9.2 |

EXAMPLE 2.7

3.0 g of N-cyclohexylidene-cyclohexylamine and 1.0 l of nitrogen are fed into the reactor described in Example 2, the catalyst temperature being 320° C.

After about 100 hours, the reaction product contains 58.0% by weight of diphenylamine, 34.0% by weight of N-cyclohexyl-aniline and 1.0% by weight of N-cyclohexylidene-aniline as well as 7.0% by weight of other by-products.

EXAMPLE 2.8

The reactor described in Example 2 is charged at a catalyst temperature of 320° C with 2.0 l of nitrogen and 3.0 g of a mixture having the composition: 33.4% by weight of N-cyclohexylidene-aniline, 37.9% by weight of N-cyclohexyl-aniline, 3.8% by weight of diphenylamine and 24.9% by weight of aniline, such as can be obtained as the intermediate runnings when a crude diphenylamine is worked up by distillation.

N-Cyclohexylidene-aniline and N-cyclohexyl-aniline are dehydrogenated on the catalyst, with relative degree of conversion of 98.5 and 99%, to give a reaction product of the following composition: 47.5% by weight of diphenylamine, 46.1% by weight of aniline, 3.2% by weight of benzene, 0.7% by weight of N-cyclohexylidene-aniline, 0.4% by weight of N-cyclohexyl-aniline and 0.5% by weight of carbazole; the amount of further impurities was 1.6% by weight.

EXAMPLE 2.9

In each case 3.0 g of the substances mentioned in Table V which follows, together with 1.0 l of nitrogen, are metered into the reactor described in Example 2; the catalyst temperature is kept at about 320° C. After a reaction time of about 200 hours, the reaction product was in each case analysed by gas chromatography; its composition is listed in Table V which follows, "remainder" indicating the sum of all the by-products, that is to say both those which can be used again as starting material for the desired product and those which cannot be used again.

weight of nickel, 11.5% by weight of chromium and 1.5% by weight of manganese, calculated as the metal in each case. Before use, the catalyst is treated with hydrogen for 2 hours at about 250° C.

EXAMPLE 4

30 ml of the catalyst obtained according to Example 3 are filled into the reaction tube described in Example 2 and the reactor is charged, in the manner described in Example 2, with, per hour, 3.0 g of N-cyclohexylidene-aniline and 1.0 l of nitrogen, the catalyst temperature being kept at about 320° C.

In the start-up period of a few days, the reaction product contains, on average, 82% by weight of diphenylamine. Subsequently, the diphenylamine content of the reaction product rises to 84.5% by weight. The reaction product also contains: 2.1% by weight of benzene, 9.4% by weight of aniline, 2.9% by weight of N-cyclohexyl-aniline, 1.0% by weight of carbazole and 2 ppm of 4-aminodiphenyl.

EXAMPLE 5

A 12% strength by weight aqueous sodium carbonate solution is added to a solution of 250.0 g of nickel sulphate, 350.0 g of manganese sulphate and 140.0 g of aluminium sulphate in 1,000 ml of water at about 80° C until the pH value reaches 8.2. After cooling the precipitate which is deposited is filtered off, washed with water until sulphate-free and suspended in 1,500 ml of water; the suspension is treated at about 85° C, whilst stirring, with an aqueous solution of 100.0 g of ammonium dichromate. After stirring for about 2 hours at this Table V

| No. | Starting substance | Reaction product (designation) | % | Unreacted starting substance (%) | Remainder (%) |
|---|---|---|---|---|---|
| 1 | N-Cyclohexylidene-2-methyl-aniline | 2-Methyl-diphenylamine | 93.0 | 3.0 | 4.0 |
| 2 | N-Cyclohexylidene-3-methyl-aniline | 3-Methyl-diphenylamine | 90.0 | | |
| 3 | N-Cyclohexylidene-4-methyl-aniline | 4-Methyl-diphenylamine | 85.0 | 7.5 | 7.5 |
| 4 | N-Cyclohexylidene-2,3-dimethylaniline | 2,3-Dimethyl-diphenylamine | 90.0 | 1.4 | 8.6 |
| 5 | N-Cyclohexylidene-3-methoxy-aniline | 4-Methoxy-diphenalamine | 85.3 | 1.7 | 13.0 |
| 6 | | | 75.0 | 9.4 | 15.6 |
| 7 | N-Cyclohexylidene-2-ethoxy-aniline | 2-Ethoxy-diphenylamine | 69.0 | 12.7 | 18.3 |
| 8 | N-Cyclohexylidene-4-ethoxy-aniline | 4-Ethoxy-diphenylamine | 64.7 | 11.3 | 24.0 |
| 9 | N-(3-Methyl-cyclohexylidene)-aniline | 3-Methyl-diphenylamine | 76.0 | 12.0 | 12.0 |
| 10 | N-(3-Methyl-cyclohexylidene)-3-methylaniline | 3,3'-Dimethyl-diphenylamine | 30.8 | 58.2 | 11.0 |
| 11 | N-(3-Methyl-cyclohexylidene)-4-methylaniline | 3,4'-Dimethyl-diphenylamine | 55.3 | 28.2 | 17.0 |

EXAMPLE 3

A 12% strength by weight aqueous sodium carbonate solution is added to an aqueous solution of 2.7 g of manganese sulphate and 12.0 g of nickel sulphate in 250 ml of water at about 80° C until the pH value reaches 8.2. After the solution has cooled, the precipitate which has deposited is separated off, washed with water until sulphate-free and suspended in 120 ml of water; this suspension is treated at about 85° C with a solution of 35.0 g of ammonium dichromate in 120 ml of water and mixture is stirred for 2 hours.

After the suspension has cooled to room temperature, the precipitate is again filtered off, dried at 120° C and pressed to give cylinders 5 mm in diameter and 5 mm in height. The catalyst thus obtained contains 41.0% by temperature, the precipitate is filtered off, dried and pressed to give cylinders 5 mm in height and 5 mm in diameter.

The catalyst thus obtained contains 11.8% by weight of nickel, 27.4% by weight of manganese, 5.8% by weight of chromium and 4.1% by weight of aluminium, in each case calculated as the metal.

Before use, the catalyst is treated with hydrogen for 2 hours at about 390° C.

EXAMPLE 6

30 ml of the catalyst obtained according to Example 5 are filled into the reaction tube described in Example 2. The reactor is charged, in the manner described in Example 2, with 3.0 g of N-cyclohexylidene-aniline and 1.0 l of nitrogen the catalyst temperature being maintained at about 320° C.

The reaction product contains 90.3% by weight of diphenylamine, 8.0% by weight of aniline, 2.4% by weight of N-cyclohexylidene-aniline, 0.7% by weight of benzene, 1.1% by weight of carbazole and 2 ppm of 4-aminodiphenyl.

EXAMPLE 7.1 (comparison example according to German Published Application No. 2,331,878)

30 ml of a $Al_2O_3$ catalyst containing 14% by weight of nickel, which has been prepared in a known manner by impregnating aluminium oxide pellets with the calculated amount of an ammoniacal solution of nickel formate, subsequently drying and treating for one hour with 30 l of hydrogen at 200° C and for 1 hour with 30 l of hydrogen at 380° C, are filled into the reaction tube described in Example 2. 12.9 g of N-cyclohexylidene-aniline, 83.0 l of nitrogen and 13.8 l of hydrogen are metered in, per hour, in the manner described in Example 2, the catalyst temperature being 370° C.

The molar ratio of N-cyclohexylidene-aniline to nitrogen to hydrogen is 1.0:46.4:7.7 and the residence time on the catalyst is 0.5 seconds.

In the first 70 hours, a reaction mixture consisting of: 86.6% by weight of N-cyclohexylidene-aniline, 5.2% by weight of diphenylamine, 4.5% by weight of N-cyclohexyl-aniline, 2.6% by weight of aniline, 0.5% by weight of carbazole and 0.4% by weight of cyclohexanone, is obtained.

In the subsequent 18 hours, a reaction mixture of the following composition: 91.9% by weight of N-cyclohexylidene-aniline, 2.0% by weight of diphenylamine, 2.5% by weight of N-cyclohexyl-aniline, 2.2% by weight of aniline, 1.0% by weight of carbazole and 0.4% by weight of cyclohexanone, is obtained.

EXAMPLE 7.2 (comparison example)

3.0 of N-cyclohexylidene-aniline and 1.0 l of nitrogen are passed over the catalyst mentioned in Example 7.1 in the reaction tube described in Example 2, the catalyst temperature being about 320° C. In this case the molar ratio of N-cyclohexylidene-aniline to nitrogen is 1:2.6.

In the first 44 hours, a reaction mixture which contains 69.0% by weight of N-cyclohexylidene-aniline, 4.0% by weight of diphenylamine, 1.8% by weight of N-cyclohexyl-aniline, 16.6% by weight of aniline, 0.1% by weight of carbazole, 4.1% by weight of cyclohexanone and 2.7% by weight of benzene, is obtained.

In the subsequent 72 hours, a reaction mixture which contains 78.5% by weight of N-cyclohexylidene-aniline, 2.9% by weight of diphenylamine, 4.3% by weight of N-cyclohexyl-aniline, 8.4% by weight of aniline, 0.1% by weight of carbazole, 3.4% by weight of cyclohexanone and 0.3% by weight of benzene, is obtained.

What is claimed is:

1. In a process for preparing a diphenylamine having the formula

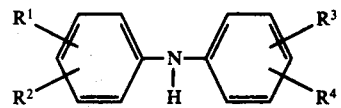

wherein
$R^1$, $R^2$, $R^3$ and $R^4$ are the same or different and are hydrogen, alkyl containing 1 to 4 carbon atoms or alkoxy containing 1 to 4 carbon atoms by catalytic dehydrogenation of a dicyclohexylamine, N-cyclohexylidene-cyclohexylamine, N-cyclohexylaniline or N-cyclohexylidene-aniline in the presence of a nickel/chromium catalyst the improvement which comprises employing as the nickel/chromium catalyst one which contains at least one member of the group manganese, aluminum and copper.

2. A process according to claim 1 wherein an N-cyclohexylidene-aniline is reacted and the same is present in admixture with N-cyclohexylidene-cyclohexylamine, dicyclohexylamine or N-cyclohexylaniline.

3. Process of claim 1 wherein the nickel/chromium catalyst contains at least one member of the group aluminum and copper, the ratio by weight of the metals nickel, chromium, aluminum and copper to one another being 40 to 60; 6.8 to 17.5; 1.5 to 8.0; 0.05 to 1.0, respectively.

4. Process of claim 1 wherein the catalyst is nickel, chromium, aluminum and copper in a weight ratio of the metals of 40 to 60; 6.8 to 17.1; 1.6 to 8.0; 0.05 to 1.0, respectively 5. Process of claim 4 wherein the metallic nickel content in the catalyst is 10 to 35 percent by weight.

6. Process of claim 4 wherein the metallic nickel content in the catalyst is 35 to 45 percent by weight.

7. Process of claim 1 wherein nickel/chromium catalyst contains at least one member of the group manganese and aluminum, the ratios by weight of the metals nickel, chromium, manganese and aluminum to one another being 10 to 50; 4 to 15; 1 to 30; 0 to 5, respectively.

8. Process of claim 1 carried out in temperature range from 250° to 400° C.

9. Process of claim 8 wherein the temperature range is 280° to 370° C.

10. Process of claim 1 carried out at atmospheric pressure.

11. Process of claim 1 carried out in a pressure range of 0.1 to 3.0 bars.

12. Process of claim 1 carried out in the presence of a gaseous diluent.

13. Process of claim 12 wherein in gaseous diluent is hydrogen, methane, natural gas or dry nitrogen.

14. Process of claim 12 wherein the gaseous diluent is used in amount of 0.1 to 10 mols per mol of nitrogen in the starting material.

15. Process of claim 14 wherein the amount of gaseous diluent is 1.0 to 5.0 mols per mol of nitrogen in the starting material.

16. Process of claim 1 wherein the reaction is carried out at a catalyst load of 0.05 g of starting material per ml of catalyst per hour.

17. Process of claim 16 wherein the load is 0.1 to 0.4 g of starging material per ml. of catalyst per hour.

18. Process of claim 16 wherein the load is 0.2 to 0.3 g of starting material per ml. of catalyst per hour.

* * * * *